(12) United States Patent
Choi et al.

(10) Patent No.: US 11,975,212 B2
(45) Date of Patent: May 7, 2024

(54) MAGNETIC-PIEZOELECTRIC MICRO ROBOT

(71) Applicant: Daegu Gyeongbuk Institute of Science and Technology, Daegu (KR)

(72) Inventors: Hong Soo Choi, Daegu (KR); Seon Hyoung Kim, Seoul (KR); Jin Young Kim, Daegu (KR); SungWoong Jeon, Daejeon (KR)

(73) Assignee: Daegu Gyeongbuk Institute of Science and Technology (KR)

( * ) Notice: Subject to any disclaimer, the term of this patent is extended or adjusted under 35 U.S.C. 154(b) by 244 days.

(21) Appl. No.: 17/499,812

(22) Filed: Oct. 12, 2021

(65) Prior Publication Data

US 2022/0152408 A1 May 19, 2022

(30) Foreign Application Priority Data

Nov. 18, 2020 (KR) ........................ 10-2020-0154182

(51) Int. Cl.
  *A61N 1/40* (2006.01)
  *A61N 1/372* (2006.01)
(52) U.S. Cl.
  CPC ......... *A61N 1/403* (2013.01); *A61N 1/37223* (2013.01)
(58) Field of Classification Search
  None
  See application file for complete search history.

(56) References Cited

U.S. PATENT DOCUMENTS

| 2012/0121712 | A1 | 5/2012 | Ciofani et al. |
| 2016/0184595 | A1* | 6/2016 | Hossainy .......... A61M 39/0247 607/116 |
| 2019/0091350 | A1* | 3/2019 | Peyman ............... A61K 49/227 |
| 2019/0351057 | A1* | 11/2019 | Pottier .................... A61P 25/00 |
| 2019/0359969 | A1 | 11/2019 | Rodriguez Murillo et al. |

FOREIGN PATENT DOCUMENTS

| EP | 1818046 | 8/2007 |
| KR | 20130001713 | 1/2013 |

OTHER PUBLICATIONS

Wikipedia.com, "Magnetism", accessed Aug. 28, 2023, https://en.wikipedia.org/wiki/Magnetism (Year: 2023).*
Marino, A. et al.; "Piezoelectric Nanoparticle-Assisted Wireless Neuronal Stimulation"; ACS Nano; vol. 9, No. 7 (2015); pp. 7678-7689 (12 pages).

(Continued)

*Primary Examiner* — Michael W Kahelin

(57) ABSTRACT

Disclosed is a magnetic-piezoelectric micro robot capable of a hyperthermia treatment, an electrotherapy and a cell therapy. The magnetic-piezoelectric micro robot includes a body and a stimulus generating layer formed at a surface of the body including a magnetic particle and a piezoelectric particle and generating heat from the magnetic particle and generating an electrical stimulus from the piezoelectric particle by an external stimulus, wherein one of a hyperthermia treatment by the magnetic particle or an electrotherapy by the piezoelectric particle is performed or both are performed simultaneously.

10 Claims, 3 Drawing Sheets

(56) References Cited

OTHER PUBLICATIONS

Liu, L. et al.; "Wireless Manipulation of Magnetic/Piezoelectric Micrometers for Precise Neural Stem-Like Cell Stimulation"; Adv. Fund. Mater. 2020, 1910108; 8 pages.

Marino, A. et al.; "Ultrasound-Activated Piezoelectric Nanoparticles Inhibit Proliferation of Breast Cancer Cells"; Scientific Reports (2018) 8:6257; Apr. 19, 2018; 13 pages.

Chen, X. et al.; "Magnetically driven piezoelectric soft microswimmers for neuron-like cell delivery and neuronal differentiation"; Mater. Horiz., 2019, vol. 6, pp. 1512-1516; Apr. 25, 2019 (5 pages).

* cited by examiner

MAGNETIC-PIEZOELECTRIC MICRO ROBOT

CROSS-REFERENCE TO RELATED APPLICATION

This application claims the benefit of Korean Patent Application No. 10-2020-0154182 filed on Nov. 18, 2020, in the Korean Intellectual Property Office, the entire disclosure of which is incorporated herein by reference for all purposes.

BACKGROUND

1. Field of the Invention

One or more example embodiments relate to a magnetic-piezoelectric micro robot.

2. Description of Related Art

Among methods of removing a cancer cell, an infiltrating method removes a cancer cell by heat generated from applying an electric current to the cancer cell. However, the infiltrating method requires an infiltration of a needle directly into a cancer cell and has an issue that it is difficult to locate the needle at an accurate point. Meanwhile, a noninfiltrating method removes a cancer cell by heating a carbon nanotube by a near infrared ray to solve the issue of the infiltrating method. However, a near infrared ray is difficult to reach deep inside a body. Thus, the noninfiltrating method has a narrow applicable scope and is difficult to apply in accordance with a size and a dispersion of a tumor.

Accordingly, there is a desire for an apparatus for treatment to destroy a cancer cell from an accurate position and selectively by a noninfiltrating method which does not require a surgery.

Meanwhile, a bacteria-based micro robot moving inside of a body with a heating apparatus using a piezoelectric phenomenon provided with a piezoelectric effect-generating wing to remove a cancer cell has been disclosed (Korea Patent Application Publication No. 10-2013-0001713). However, the cited invention is based on bacteria and thus has a limit in controlling a location precisely and performing an electrotherapy and a hyperthermia treatment.

The above description is information the inventor(s) acquired during the course of conceiving the present disclosure, or already possessed at the time, and is not necessarily art publicly known before the present application was filed.

SUMMARY

An aspect provides a magnetic-piezoelectric micro robot capable of a hyperthermia treatment and an electrotherapy which may effectively stimulate and transfer a cell, destroy only a target cancer cell during an anticancer therapy, and minimize a damage to a normal cell.

The technical tasks obtainable from the present disclosure are non-limited by the above-mentioned technical tasks. And, other unmentioned technical tasks can be clearly understood from the following description by those having ordinary skill in the technical field to which the present disclosure pertains.

A magnetic-piezoelectric micro robot according to an embodiment will be described.

The magnetic-piezoelectric micro robot may be formed on a body and a surface of the body, include a magnetic particle and a piezoelectric particle, include a stimulus generating layer generating heat from the magnetic particle and generating an electrical stimulus from the piezoelectric particle by an external stimulus, and perform any one of a hyperthermia treatment by the magnetic particle or an electrotherapy by the piezoelectric particle or both simultaneously.

The external stimulus may include a first source to apply a magnetic field to the magnetic particle and a second source to apply a mechanical stimulus to the piezoelectric particle.

The stimulus generating layer may be formed by mixing the magnetic particle and the piezoelectric particle. The stimulus generating layer may be formed of a piezoelectric layer including the piezoelectric particle only and a magnetic layer including the magnetic particle only. The stimulus generating layer may be formed by laminating the piezoelectric layer onto the magnetic layer.

The body may be formed of any one material of a polymer, a cluster, a metal and a composite material.

Additional aspects of example embodiments will be set forth in part in the description which follows and, in part, will be apparent from the description, or may be learned by practice of the disclosure.

According to example embodiments, since a magnetic-piezoelectric micro robot includes a magnetic particle and a piezoelectric particle, a hyperthermia treatment by the magnetic particle and an electrotherapy by the piezoelectric particle may be performed. In addition, either one of a hyperthermia treatment or an electrotherapy may be selectively performed, or both may be performed simultaneously.

In addition, the magnetic-piezoelectric micro robot may provide a three-dimensional (3D) position control by an external magnetic field and may be effectively transferred to a target position inside of a body. Thus, the micro robot may be safely and precisely transferred inside of a patient.

In addition, the magnetic-piezoelectric micro robot may provide a multifunctional micro robot system applicable to various application fields in cell therapy such as inhibiting a cancer cell proliferation, stimulating a neuron and a muscle cell, promoting dopamine secretion inside of a body.

Conventional cell stimulation technology is difficult to selectively stimulate desired sites only and stimulates a cell by only a single method without considering a method of applying inside of a body. On the contrary, the magnetic-piezoelectric micro robot may provide various cell stimulation methods and a 3D position control. The effects of the magnetic-piezoelectric micro robot are not limited to the above-mentioned effects, and other unmentioned effects can be clearly understood from the following description by one of ordinary skill in the art.

DETAILED DESCRIPTION

Figure 1:
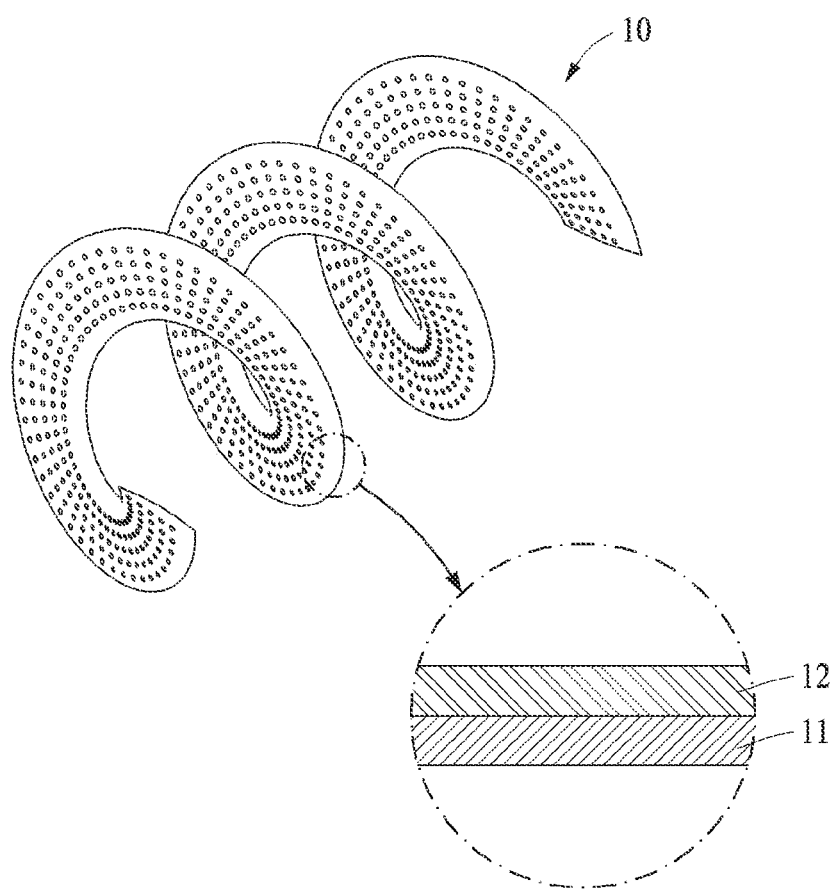
FIG. 1 is a perspective view of a magnetic-piezoelectric micro robot according to an example embodiment.

Hereinafter, example embodiments will be described in detail with reference to the accompanying drawings. However, various alterations and modifications may be made to the example embodiments. Here, the example embodiments are not construed as limited to the disclosure. The example embodiments should be understood to include all changes, equivalents, and replacements within the idea and the technical scope of the disclosure.

The terminology used herein is for the purpose of describing particular example embodiments only and is not to be limiting of the example embodiments. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the example embodiments with reference to the accompanying drawings, like reference numerals refer to like constituent elements and a repeated description related thereto will be omitted. In the description of example embodiments, detailed description of well-known related structures or functions will be omitted when it is deemed that such description will cause ambiguous interpretation of the present disclosure.

Also, in the description of the components, terms such as first, second, A, B, (a), (b) or the like may be used herein when describing components of the present disclosure. These terms are used only for the purpose of discriminating one constituent element from another constituent element, and the nature, the sequences, or the orders of the constituent elements are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

The constituent element, which has the same common function as the constituent element included in any one embodiment, will be described by using the same name in other embodiments. Unless disclosed to the contrary, the configuration disclosed in any one embodiment may be applied to other embodiments, and the specific description of the repeated configuration will be omitted.

Figure 2A:
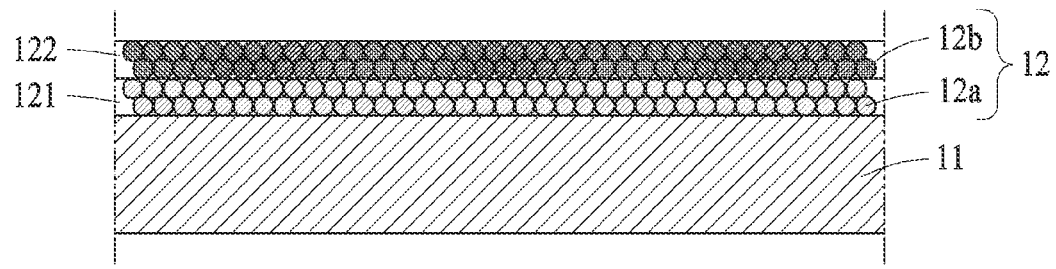
FIGS. 2A and 2B illustrate examples of stimulus generating layers of the magnetic-piezoelectric micro robot in FIG. 1.
Figure 2B:
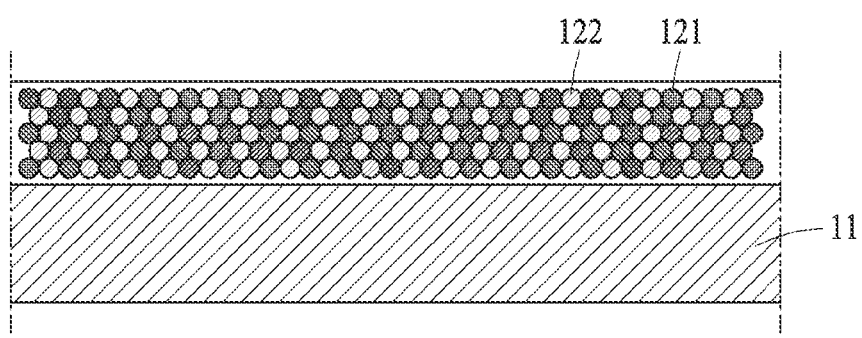
Figure 3:
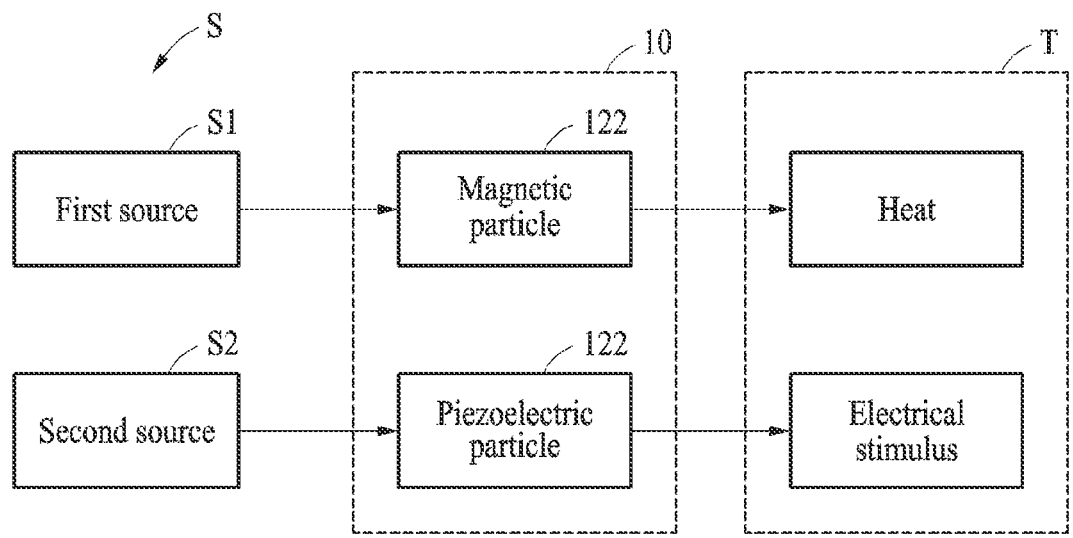
FIG. 3 is a block diagram illustrating an operation of the magnetic-piezoelectric micro robot in FIG. 1.

Hereinafter, a magnetic-piezoelectric micro robot 10 will be described with reference to FIGS. 1 to 4. For reference, FIG. 1 is a perspective view of the magnetic-piezoelectric micro robot 10 according to an embodiment. FIGS. 2A and 2B illustrate examples of stimulus generating layers of the micro robot 10 in FIG. 1. FIG. 3 is a block diagram illustrating an operation of the micro robot 10 in FIG. 1.

A "micro robot" described herein may refer to a micro-sized robot for a medical purpose. However, the micro robot is not limited to a micro-sized robot, and may include a nano-sized robot, and a smaller sized robot.

The micro robot 10 may include a body 11 formed of any one material of a polymer, a cluster, a metal or a composite material, and a stimulus generating layer 12 including a micro-sized or nano-sized magnetic particles 121 and a nano-sized piezoelectric particles 122.

The body 11 may have a three-dimensional (3D) porous structure. For example, the body 11 may have any one of a spiral structure, a spherical structure, a 3D spheroid structure, a 3D needle structure, and a cuboid structure.

A surface area of the body 11 may be increased due to the porous structure of the body 11. Thus, the stimulus generating layer 12 may be more effectively operated by an external stimulus S. In addition, in case of mounting a cell 13 to the micro robot 10 which will be described below, a larger number of cells 13 may be stably mounted.

A three-dimensional printing method or a microfluidic channel-based manufacturing method or a lithography method may be used for the body 11. In addition, various methods may be used to form the micro-sized or nano-sized body 11.

In addition, the body 11 may be loaded with a medication to apply to a target T. For example, the body 11 may load a medication inside or may be shaped to impregnate a medication by immersing a polymer forming the body 11 in the medication. The medication in the micro robot 10 may be omitted.

The stimulus generating layer 12 may include the magnetic particles 121 and the piezoelectric particles 122 and may be formed at a surface of the body 11 in a predetermined thickness.

Here, as shown in FIG. 2A, the stimulus generating layer 12 may be formed by laminating a magnetic layer 12a including the magnetic particles 121 only and a piezoelectric layer 12b including the piezoelectric particles 122 only. Although the drawing illustrates that the piezoelectric layer 12b is formed on the magnetic layer 12a, the magnetic layer 12a may be formed on the piezoelectric layer 12b. Alternatively, laminating a plurality of magnetic layers 12a and a plurality of piezoelectric layers 12b alternately may also be possible.

Alternatively, as shown in FIG. 2B, the stimulus generating layer 12 may include a single layer by mixing the magnetic particles 121 and the piezoelectric particles 122.

When the external stimulus S is applied to the micro robot 10, heat and an electrical stimulus may be generated from the stimulus generating layer 12 and a hyperthermia treatment and an electrotherapy may be performed to a target.

Referring to FIG. 3, the magnetic particles 121 may allow a hyperthermia treatment to the target T by generating heat by the external stimulus S. Furthermore, the external stimulus S may include a first source S1 which applies a magnetic field to the magnetic particles 121 to generate heat.

The magnetic particles 121 may include a biocompatible particle, for example, $Fe_3O_4$ particle. However, a type of the magnetic particles 121 may substantially include various micro-sized or nano-sized particles with magnetism.

Alternatively, the magnetic particles 121 may serve as a driver to rotate and transfer the micro robot 10 to the target T by a magnetic field applied from an outside.

The piezoelectric particles 122 may allow a treatment by an electrical stimulus for the target T by generating an electrical stimulus by the external stimulus S. Furthermore, the external stimulus S may include a second source S2 to generate an electrical stimulus from the piezoelectric particles 122. Here, since the piezoelectric particles 122 may convert mechanical energy into electrical energy, the second source S2 may apply a mechanical stimulus.

For reference, a direct piezoelectric effect may refer to generating an electric current by applying a force or a stress to the piezoelectric particles 122. On the contrary, a converse piezoelectric effect may refer to generating a stress and a displacement when an electric current is applied to the piezoelectric particles 122. That is, the piezoelectric particles 122 may allow an electrotherapy to the target T including a cancer cell by using a direct piezoelectric effect which generates an electrical stimulus by a mechanical stimulus.

However, the second source S2 may substantially include various sources, such as ultrasonic waves, capable of applying a mechanical stimulus to the piezoelectric particles 122.

Figure 4:
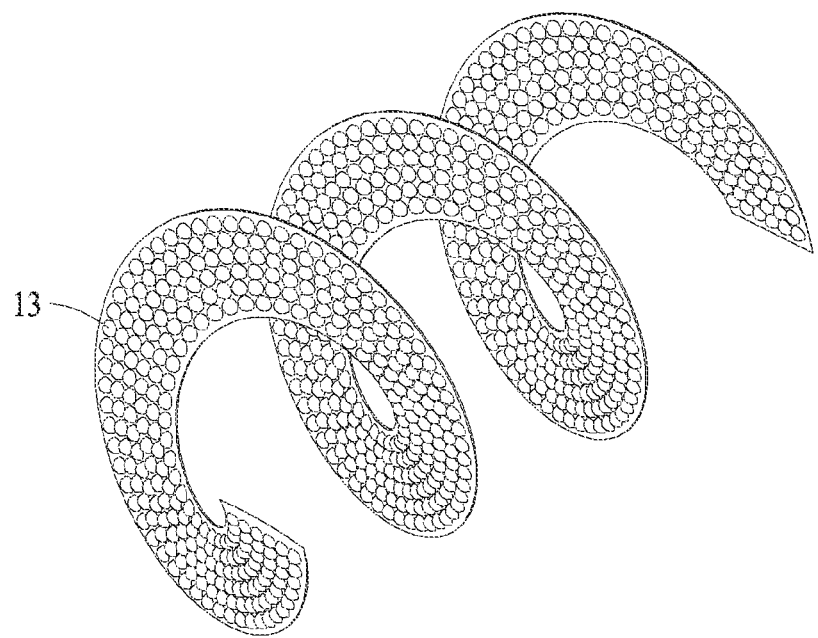
FIG. 4 is a perspective view of a magnetic-piezoelectric micro robot according to another example embodiment.

Meanwhile, referring to FIG. 4, the micro robot 10 may culture the cell 13 on a surface of the body 11. For reference, FIG. 4 is a perspective view of the magnetic-piezoelectric micro robot 10 according to another example embodiment.

The micro robot 10 illustrated in FIG. 4 is the same as the micro robot 10 according to the example embodiments described above, except that the cell 13 is cultured on a surface of the micro robot 10. Thus, a duplicate description will be omitted.

The micro robot 10 may transfer the cell 13 to the target T by three-dimensionally culturing a plurality of cells 13 on a surface of the micro robot 10.

That is, when the external stimulus S is applied to the micro robot 10, either a hyperthermia treatment or an electrotherapy may be performed or both may be performed simultaneously to the target T. In addition, a cell therapy may be simultaneously performed by using the cell 13 transferred by the micro robot 10.

Here, the cell 13 may be 3D cultured at a surface of the body 11 by simultaneously culturing the micro robot 10 and a predetermined cell 13 at an ultra-low attachment (ULA) surface-treated U-bottom well. In addition, the cell 13 may be mounted on the body 11 in various ways.

According to the example embodiments, since the magnetic-piezoelectric micro robot 10 may include the magnetic particles 121 and the piezoelectric particles 122, one of a hyperthermia treatment by heat generated from the magnetic particles 121 by the external stimulus S applied from an outside or an electrotherapy by an electrical stimulus generated from the piezoelectric particles 122 may be performed or both may be performed simultaneously. In addition, the micro robot 10 may provide a 3D position control inside of a body by a magnetic field applied from an outside and may be transferred wirelessly to the target T. Thus, the micro robot 10 may be transferred inside of a patient safely and precisely.

In addition, since the micro robot 10 may attach the cell 13 to a surface of the body 11, the micro robot 10 may transfer the cell 13 to the target T and perform a targeted therapy. Thus, an efficiency in treatment may be enhanced since a sufficient number of cells 13 may be transferred.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

What is claimed is:

1. A magnetic-piezoelectric micro robot comprising:
a body; and
a stimulus generating layer formed at a surface of the body and comprising a magnetic particle operable to generate heat upon receiving a first external stimulus, and a piezoelectric particle operable to generate an electrical stimulus upon receiving a second external stimulus,
wherein the stimulus generating layer is operable to facilitate at least one of a hyperthermia treatment by the magnetic particles, or
an electrotherapy treatment by the piezoelectric particle, or
both the hyperthermia treatment and the electrotherapy treatment simultaneously, and wherein the body and the magnetic particle are configured to facilitate three-dimensional position control and movement of the micro robot in response to an applied magnetic field.

2. The magnetic-piezoelectric micro robot of claim 1, wherein:
the first external stimulus is generated by a first source that applies a magnetic field to the magnetic particle; and
the second external stimulus is generated by a second source that applies a mechanical stimulus to the piezoelectric particle.

3. The magnetic-piezoelectric micro robot of claim 1, wherein the stimulus generating layer comprises a single layer including both the magnetic particle and the piezoelectric particle.

4. The magnetic-piezoelectric micro robot of claim 1, wherein the stimulus generating layer comprises a piezoelectric layer comprising the piezoelectric particle only and a magnetic layer comprising the magnetic particle only.

5. The magnetic-piezoelectric micro robot of claim 4, wherein the stimulus generating layer comprises the piezoelectric layer laminated onto the magnetic layer.

6. The magnetic-piezoelectric micro robot of claim 1, wherein the body is formed of any one or more materials comprising a polymer, a cluster, a metal or a composite material.

7. The magnetic-piezoelectric micro robot of claim 1, wherein a cell is mounted onto a surface of the stimulus generating layer.

8. The magnetic-piezoelectric micro robot of claim 7, wherein the cell is mounted onto a surface of the body via three-dimensional culturing.

9. The magnetic-piezoelectric micro robot of claim 1, wherein the stimulus generating layer is operable to facilitate:
a hyperthermia treatment by the magnetic particle;
an electrotherapy treatment by the piezoelectric particle; or
both hyperthermia treatment and the electrotherapy treatment, and wherein the hyperthermia treatment and the electrotherapy treatment facilitate destroying only targeted cancer cells, without destroying normal cells.

10. The magnetic-piezoelectric micro robot of claim 1, wherein the hyperthermia treatment and the electrotherapy treatment facilitate destroying only targeted cancer cells without infiltrating the targeted cancer cells.

* * * * *